United States Patent
Poon et al.

(10) Patent No.: US 8,690,609 B2
(45) Date of Patent: Apr. 8, 2014

(54) METHOD, APPARATUS AND SYSTEM FOR POSITIONING AND HOLDING ELECTRICAL CONTACTS, SEALS AND RELATED COMPONENTS

(75) Inventors: Daniel D. Poon, Foothill Ranch, CA (US); James C. Biggs, Minneapolis, MI (US)

(73) Assignee: Bal Seal Engineering, Inc., Foothill Ranch, CA (US)

( * ) Notice: Subject to any disclaimer, the term of this patent is extended or adjusted under 35 U.S.C. 154(b) by 59 days.

(21) Appl. No.: 13/476,752

(22) Filed: May 21, 2012

(65) Prior Publication Data
US 2012/0315798 A1 Dec. 13, 2012

Related U.S. Application Data

(60) Provisional application No. 61/495,259, filed on Jun. 9, 2011.

(51) Int. Cl.
*H01R 24/00* (2011.01)
(52) U.S. Cl.
USPC .......................................................... 439/668
(58) Field of Classification Search
USPC ......... 439/668–669, 271, 248, 843, 675, 931, 439/840–841
See application file for complete search history.

(56) References Cited

U.S. PATENT DOCUMENTS

| 4,072,154 | A  | * | 2/1978  | Anderson et al. | 607/37  |
|-----------|----|---|---------|-----------------|---------|
| 7,108,549 | B2 | * | 9/2006  | Lyu et al.      | 439/587 |
| 7,195,523 | B2 | * | 3/2007  | Naviaux         | 439/827 |
| 7,429,199 | B2 | * | 9/2008  | Burgess         | 439/841 |
| 7,654,843 | B2 | * | 2/2010  | Olson et al.    | 439/248 |
| 7,822,477 | B2 | * | 10/2010 | Rey et al.      | 607/37  |
| 8,091,226 | B2 | * | 1/2012  | Sjostedt et al. | 29/876  |
| 8,500,499 | B2 | * | 8/2013  | Drew et al.     | 439/843 |
| 2003/0163171 | A1 | * | 8/2003 | Kast et al.    | 607/36  |
| 2008/0246231 | A1 | * | 10/2008 | Sjostedt et al. | 277/641 |
| 2008/0255631 | A1 | * | 10/2008 | Sjostedt et al. | 607/37 |
| 2009/0258519 | A1 | * | 10/2009 | Dilmaghanian et al. | 439/271 |

* cited by examiner

*Primary Examiner* — Jean F Duverne
(74) *Attorney, Agent, or Firm* — Klein, O'Neill & Singh, LLP

(57) ABSTRACT

A header assembly and method to incorporate electrical contacts and seals into a header are described. The header and method include properly positioning a stack of electrical contact housings and seals or seal assemblies in the header and maintaining the electrical contact housings and the seals in the header with pins inserted in the header from outside the header through axially arranged holes in the header to interface corresponding grooves of the electrical contact housings.

15 Claims, 4 Drawing Sheets

METHOD, APPARATUS AND SYSTEM FOR POSITIONING AND HOLDING ELECTRICAL CONTACTS, SEALS AND RELATED COMPONENTS

CROSS-REFERENCE TO RELATED APPLICATION

This is a Regular Utility application of Provisional application No. 61/495.259, filed Jun. 9, 2011; the contents of which are expressly incorporated herein by reference.

FIELD

The present disclosure relates to methods, devices and systems for positioning and holding electrical contacts, seals and related components in a housing. For example, electrical contacts, seals, and related components may be positioned in a header of an implantable medical device that can include an Implantable Pulse Generators (IPG) used in Cardiac Rhythm Management and Neuro-stimulation devices.

BACKGROUND

Traditional methods of manufacturing a header assembly for Implantable Pulse Generators (IPG) used in Cardiac Rhythm Management and Neuro-stimulation devices involve fixing electrical contacts that interface with the stimulation lead on a tooling pin and elastomeric separation seals between the contacts by over-molding the assembly with a liquid plastic resin. The resin solidifies to encapsulate the contact and seal assembly holding the components in place thereby making up the header assembly. With this method. the liquid resin may leak into the electrical contacts and the seals. If the resin leaks into the electrical contacts and seals or the header molding process does not work well for any reason, the entire IPG must be rejected.

SUMMARY

A header assembly and method to incorporate electrical contacts and seals into a header includes properly positioning a stack of electrical contact housings and seals or seal assemblies in the header and maintaining the electrical contact housings and the seals in the header with pins inserted in the header from outside the header through axially arranged holes in the header to interface corresponding grooves of the electrical contact housings. The header may be a pre-molded plastic header.

An aspect of the present disclosure includes a header assembly for an implantable device, the header assembly comprising a header having a bore; at least one electrical contact ring located in the bore; at least one seal located in the bore; and at least one locator pin inserted into the header through an opening in the header, which is spaced from an inlet opening of the header. In one example, the pin is configured to interface with the electrical contact ring to retain the electrical contact ring and the seal in the bore of the header.

In some embodiments, the header is made from a plastic material.

In some embodiments, the at least one electrical contact ring includes an outer groove in contact with the pin.

In some embodiments, the at least one electrical contact ring includes an annular inner groove and a spring positioned in the groove.

In some embodiments, the spring is a canted coil spring.

In some embodiments, the annular groove comprises two side walls and a bottom wall.

In some embodiments, the at least one contact ring mechanically engages the at least one seal.

In some embodiments, the at least one seal comprises at least one inner rib for sealing against a lead.

A further aspect of the present disclosure is a method of making a header assembly for an implantable device. The method can comprising forming a header, the header having an inlet and a bore; installing at least one electrical contact ring and at least one seal in the bore of the header; and retaining the electrical contact ring and the seal in the bore of the header with a pin inserted in the header through a corresponding opening in the header spaced from the inlet to interface with the electrical contact ring.

In certain embodiments, the method wherein the header is constructed from plastic.

In certain embodiments, the method can further comprise the step of forming an outer groove in the at least one electrical contact ring to receive the pin.

In certain embodiments, the method wherein the at least one electrical contact ring includes an annular inner groove and a spring positioned in the groove.

In certain embodiments. the method wherein the spring is a canted coil spring.

In certain embodiments, the method wherein the annular groove comprises two side walls and a bottom wall located therebetween.

In certain embodiments, the method wherein the header has a parting line and is made from at least two housing sections.

BRIEF DESCRIPTION OF DRAWINGS

These and other features and advantages of the present devices, systems, and methods will become appreciated as the same becomes better understood with reference to the specification, claims and appended drawings wherein:

DETAILED DESCRIPTION

The detailed description set forth below in connection with the appended drawings is intended as a description of the presently preferred embodiments of in-line connector stacks and headers and related methods provided in accordance with aspects of the present devices, systems, and methods and is not intended to represent the only forms in which the present devices, systems, and methods may be constructed or utilized. The description sets forth the features and the steps for constructing and using the embodiments of the present devices, systems, and methods in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

Figure 1:
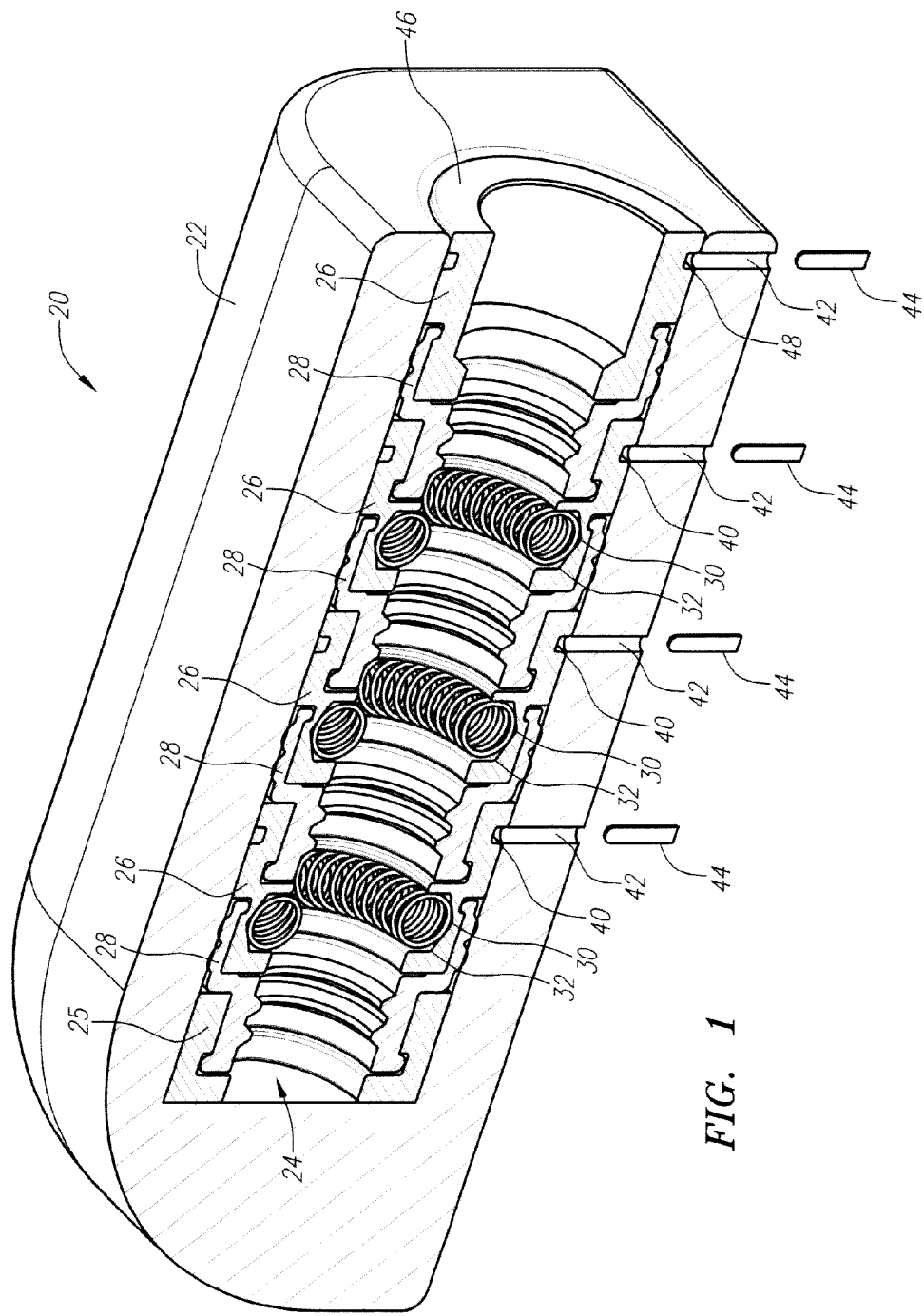
FIG. 1 shows a perspective cutaway view of a header assembly for an Implantable Pulse Generators (IPG) according to one embodiment.

Referring to FIG. 1, a cutaway view of a header assembly 20 according to an exemplary embodiment is shown. The header assembly 20 may be used in a variety of applications. In the embodiments described herein, the header assembly is used for Implantable Pulse Generators (IPG) used in Cardiac Rhythm Management and Neuro-stimulation. The header assembly 20 includes a header 22 having a bore 24, in which a leading cap 25, one or more generally annular electrical contact rings 26 and one or more generally annular seals 28 are mounted. Because the header assembly 20 is configured for implanting in a living body, the seals 28 prevent bodily fluids from reaching the electrical contacts 26. For example, the seals 28 seal exteriorly against the header 22 and seal interiorly against a lead cable when the same is inserted into the inlet opening of the common bore 24. Each electrical contact ring 26 may accommodate at least one spring, such as a radial or an axial canted coil spring 30, in at least one annular groove 32, which comprises two side walls and a bottom wall located therebetween. In another example, at least one of the side walls is formed, defined, or provided by a wall section of an adjacent annular seal 28. A lead or lead cable (not shown), which may be generally in the shape of a pin, rod or the like can be inserted into the bore 24 to contact the springs 30 to provide electrical current flow between the lead and the electrical contact rings 26. In practice, the contract rings 26 are wired to or in electrical communication with an enclosed circuit located inside a sealed housing, also known as a can, which has control circuits and power for sending signals to the lead cable. The springs 30 provide a holding connection between the lead and the electrical contact ring 26. Details of the electrical contacts, seals, canted coil springs and/or the holding, latching or locking of pins, rods, or the like with a canted coil springs are provided in U.S. Patent Application Publications US 2008/0254670; US 2008/0255631; US 2009/0258519; US 2010/0123291; US 2010/0267265, the entire disclosures of which are explicitly incorporated herein by reference.

Figure 3:
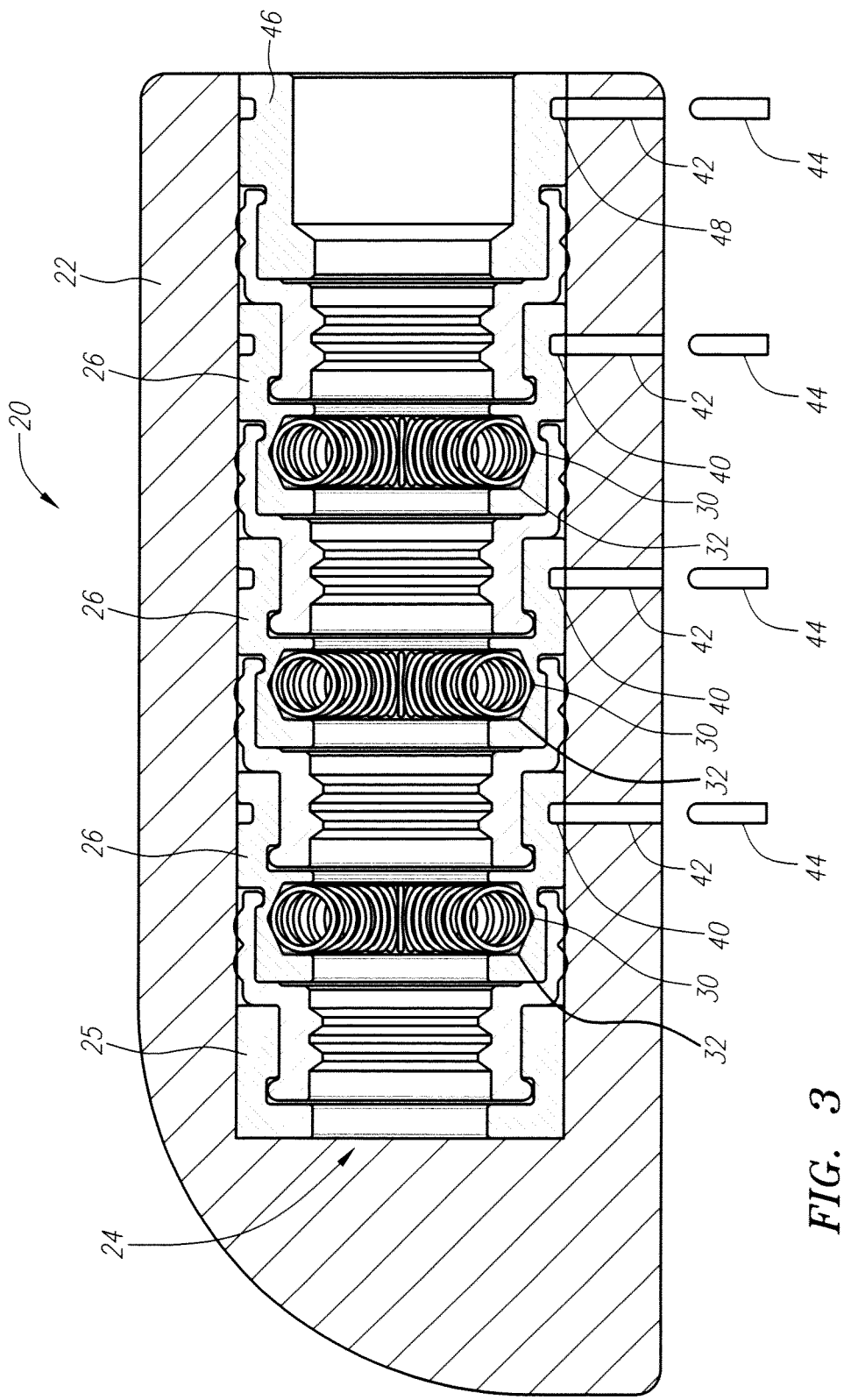
FIG. 3 shows a cross-sectional view of the header assembly of FIG. 1.

The header 20 is a pre-molded plastic part according to the embodiment described herein, but may be constructed from any type of biocompatible material. For example, the header may be made from an elastomer or thermoplastic elastomer (TPE). The header may comprise a single piece housing or formed from two or more housing sections have a horizontal parting line, a vertical parting line, or both, where the two or more housing sections are joined. An outside surface of each electrical contact ring 26 includes outer grooves, channels, pockets, or slots 40, which are shown in FIGS. 1 and 3 to be annular outer grooves 40. The header 22 includes axially arranged holes 42 that align or correspond in location to the location of the grooves 40 when the electrical contact rings 26 and the seals 28 are installed in the bore 24. The holes may be formed during the molding of the header 20 or post-formed, such as drilled, after the molding process. The header assembly 20 includes locator pins 44 that are sized so as to be press fit in the holes 42 and interface with the grooves 40. The locator pins 44 may be rigid and constructed from steel, titanium, or other rigid biocompatible metals or plastics. The holes 42 have slightly smaller internal diameters than the outside diameter of the pins 44 to provide adequate sealing. In one example, the pins and the axially arranged holes are in an interference fit. In another embodiment, the holes are about the same size as the pins or slightly larger than the pins and are sealed after placement of the pins into the holes. In still yet another example, the grooves 40 for engaging the pins are formed on the seals 28, or both the contact rings and the seals.

The header assembly 20 is assembled by inserting and properly positioning the leading cap 25, electrical contact rings 26 and the seals 28 in the bore 24 of the header 22. Once the electrical contact rings 26 and seal assemblies 28 are properly positioned axially so that the grooves 40 are aligned with the holes 42, the locating pins 44 are inserted in the holes 42 to interface with the grooves 40. The locator pins 44 can locate and hold each electrical contact ring 26 in a proper axial position relative to the header. Additionally, the positioning of the electrical contact rings 26 maintains the proper sealing function between the electrical contact rings 26 and the seals 28 to prevent leakage of body fluids that would interfere with the IPG electrical circuits. Furthermore, the interface of the pins 44 with the grooves 32 prevents axial displacement of the electrical contact rings 26 and the seals 28, or compression of these parts, when the lead is inserted in the bore 24 for engagement with the springs 30. In other words, engagements between the pins 44 and the grooves 32 are configured to prevent or limit axial shifting of the various components in the direction of insertion of the lead cable when the lead cable is inserted into the bore 24. Shifting, if it occurs, is typically due to the inner or inwardly extending ribs 37 of the annular seals 28 gripping the exterior surface of the lead cable (not shown) as the lead cable is inserted into the bore 24. Thus, aspects of the present apparatus, device, and assembly comprise an in-line connector stack located in a header and wherein the in-line connector stack is secured against axial movement relative to the header by at least one pin engaging a groove formed on the in-line connector stack. In specific embodiments, plurality of pins are engaged with plurality of corresponding grooves on the in-line connector stack to secure the in-line connector stack from axial movement relative to the header. In one example, each contact ring has a groove for engaging a pin, which may alternatively be referred to as an anchor pin.

Figure 2:
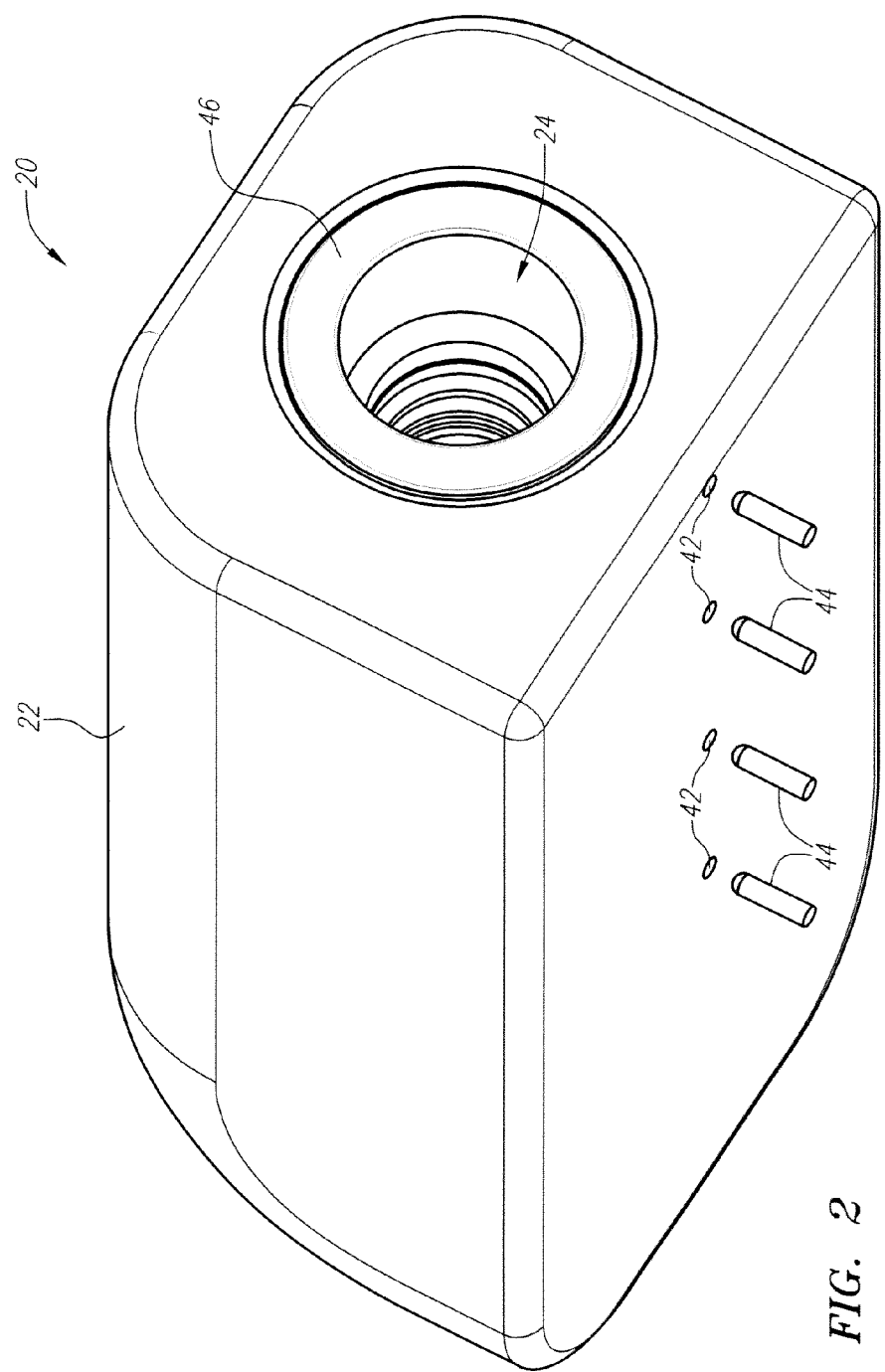
FIG. 2 shows another perspective view of the header assembly of FIG. 1.

In one embodiment shown in FIGS. 1 and 2, the locating pins 44 are pressed into the pre-molded header 22 from the bottom of the header 22 since the header 22 may be bonded to the top of the IPG, which may contain battery and control circuits for convenient connection to the pins 44. However, the pins 44 may be located at any location on the header 22. In yet other embodiments, the pins are located along different sections of the header 22. For example, two pins may be located on the bottom of the header while two other pins located on the top of the head. Because the pins 44 are press fit in the holes 42, the pins 44 are restrained by the resilient properties of the header 22. In a particular embodiment, the header is made from a plastic material. Where the header is made from plastic, a large restraining force, or a tight press fit may not be necessary since the plastic material, relatively speaking, has greater structural integrity than other prior art header materials. In addition to locating and holding the components within the plastic header 20, the pins 44 also prevent axial distortion of the electrical contact rings 26 and seals 28 when the lead is inserted in the header 20. The stack which is formed by the leading cap 25, electrical contact rings 26 and seals 28 is capped by an end cap 46. The end cap 46 may also include a groove, pocket, or slot, for engaging with a locating pin. The groove on the end cap 46 is shown in FIGS. 1 and 3 to be an annular groove 48. The lead may also have a set or secure section for securing the lead in the bore 24 with a set screw with either the leading cap 25 or the end cap 46. Both the lead set section and the cap 46 can be pinned with pins 44 to the header 22 (only the cap 46 is shown to be pinned in FIGS. 1-3).

Figure 4:
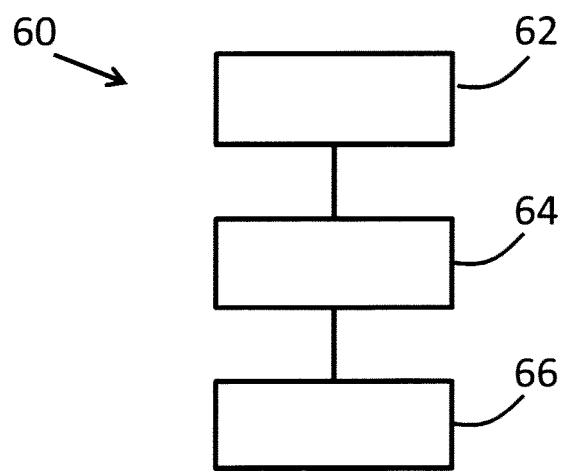
FIG. 4 is a process flow diagram showing an exemplary method of making a header assembly for an implantable device.

FIG. 4 depicts an exemplary method of making a header assembly for an implantable device 60 provided in accordance with aspects of the present disclosure. In one example, the method 60 comprises the steps for forming a header at step

62. In a particular embodiment, this can involve molding a header, such as that shown in FIG. 1, with a plastic material. In other example, the header is molded using different materials, such as an elastomer or a TPE. The header may include an inlet and a bore for receiving a lead cable.

At 64, the method includes the step of installing at least one electrical contact ring and at least one seal in the bore of the header. In other examples, multiple contact rings and multiple seals are installed in the header. At 66, the method includes the step of retaining the electrical contact ring or rings and the seal or seals in the bore of the header with a corresponding number of pins inserted in the header through a corresponding number of openings formed in the header. The openings are spaced from the inlet to interface with the electrical contact ring.

Although limited embodiments of in-line connector assemblies and headers and their components have been specifically described and illustrated herein, many modifications and variations will be apparent to those skilled in the art. For example, the various seal configurations may differ, the contact rings may differ, the end cap may differ or leading cap may differ. For example, the seals may only have a single inward projection to seal against a lead cable, the contact ring may embodiment a simple ring without side walls forming a groove. etc. For example, an in-line connector embodiment may incorporate contact rings with external grooves for engaging corresponding locating pins but wherein the remaining features of the seals and the contact rings, such as how the seals and the contact rings mechanically engage one another or seal against the header, may differ from that shown. In some examples, the seals and contact rings may resemble those disclosed in Publication Nos. US2011/0059639; US2008/0246231; and US2010/0123291 but wherein an exterior locating groove is formed on at least one contact ring. Preferably, each contact ring of the alternative contact rings incorporates an exterior locating groove for engaging a locating pin. In yet another embodiment. a device for securing leads into in-line connector devices according to U.S. Pat. No. 8,092,260 is incorporated instead of a set screw arrangement.

Furthermore, it is understood and contemplated that features specifically discussed for one in-line connector and header embodiment may be adopted for inclusion with another in-line connector and header embodiment, provided the functions are compatible. Accordingly, it is to be understood that the in-line connector assemblies and headers and their components constructed according to principles of the disclosed device, system, and method may be embodied other than as specifically described herein. The disclosure is also defined in the following claims.

What is claimed is:

1. A header assembly for an implantable device, the header assembly comprising:
   a header having a bore;
   at least one electrical contact ring located in the bore, said at least one electrical contact ring comprising an exterior surface;
   at least one seal located in the bore, said at least one seal comprising an exterior surface;
   at least one locator pin having a first end and a second end inserted into the header through an opening in the header, which is spaced from an inlet opening of the header, to interface with the electrical contact ring to retain the electrical contact ring and the seal in the bore of the header; and
   wherein the locator pin is pressed fit into the header, the at least one electrical contact, or both without a weld to secure the at least one electrical contact axially relative to the header.

2. The header assembly of claim 1, wherein the header is made from a plastic material.

3. The header assembly of claim 1, wherein the at least one electrical contact ring includes an outer groove in contact with the locator pin.

4. The header assembly of claim 1, wherein the at least one electrical contact ring includes an annular inner groove and a spring positioned in the groove.

5. The header assembly of claim 4, wherein the spring is a canted coil spring.

6. The header assembly of claim 4, wherein the annular groove comprises two side walls and a bottom wall.

7. The header assembly of claim 1, wherein the at least one contact ring mechanically engages the at least one seal.

8. The header assembly of claim 1, wherein the at least one seal comprises at least one inner rib for sealing against a lead.

9. A method of making a header assembly for an implantable device, the method comprising:
   forming a header, the header having an inlet and a bore;
   installing at least one electrical contact ring comprising an exterior surface and at least one seal comprising an exterior surface in the bore of the header; and
   retaining the electrical contact ring and the seal in the bore of the header with a locator pin inserted in the header through a corresponding opening in the header spaced from the inlet to interface with the electrical contact ring; and
   wherein the locator pin engages a groove inside the header without a weld to axially locate the at least one electrical contact ring, the at least one seal, or both.

10. The method of claim 9, wherein the header is constructed from plastic.

11. The method of claim 9, further comprising forming an outer groove in the at least one electrical contact ring to receive the locator pin.

12. The method of claim 9, wherein the at least one electrical contact ring includes an annular inner groove and a spring positioned in the groove.

13. The method of claim 12, wherein the spring is a canted coil spring.

14. The method of claim 12, wherein the annular groove comprises two side walls and a bottom wall located therebetween.

15. The method of claim 9, wherein the header has a parting line and is made from at least two housing sections.

* * * * *

UNITED STATES PATENT AND TRADEMARK OFFICE
CERTIFICATE OF CORRECTION

| | | |
|---|---|---|
| PATENT NO. | : 8,690,609 B2 | Page 1 of 1 |
| APPLICATION NO. | : 13/476752 | |
| DATED | : April 8, 2014 | |
| INVENTOR(S) | : Poon et al. | |

It is certified that error appears in the above-identified patent and that said Letters Patent is hereby corrected as shown below:

In the Specification

In column 1, line 10, delete "61/495.259," and insert -- 61/495,259, --, therefor.

In column 1, line 33, delete "method." and insert -- method, --, therefor.

In column 2, line 24, delete "embodiments." and insert -- embodiments, --, therefor.

In column 5, line 25, delete "groove." and insert -- groove, --, therefor.

In column 5, line 37, delete "embodiment." and insert -- embodiment, --, therefor.

Signed and Sealed this
Twenty-first Day of October, 2014

Michelle K. Lee
*Deputy Director of the United States Patent and Trademark Office*